United States Patent [19]

Nishiyama et al.

[11] Patent Number: 5,683,891
[45] Date of Patent: Nov. 4, 1997

[54] METHOD FOR PRODUCING EXOGENOUS PROTEIN

[75] Inventors: Kiyoto Nishiyama, Kikuchi; Yuji Ishikawa, Kumamoto; Kazuhiko Kimachi, Kikuchi-gun; Hiroaki Maeda; Sachio Tokiyoshi, both of Kumamoto, all of Japan

[73] Assignee: Juridical Foundation The Chemo-Sero Therapeutic Research Institute, Kumamoto, Japan

[21] Appl. No.: 436,462

[22] PCT Filed: Nov. 25, 1993

[86] PCT No.: PCT/JP95/01723

§ 371 Date: May 26, 1995

§ 102(e) Date: May 26, 1995

[87] PCT Pub. No.: WO94/12658

PCT Pub. Date: Jun. 9, 1994

[30] Foreign Application Priority Data

Nov. 28, 1992 [JP] Japan ............................ 4-341256

[51] Int. Cl.[6] ........................... C07K 16/44; C12P 21/08; C12N 15/06; C12N 15/13
[52] U.S. Cl. ................... 435/69.1; 435/328; 435/346; 435/70.2; 530/387.3; 935/103; 935/109; 935/34
[58] Field of Search ............... 530/387.3, 388.1, 530/808, 809; 935/89, 93, 103, 109, 34; 435/240.2, 172.2, 70.21, 69.1, 328, 346

[56] References Cited

U.S. PATENT DOCUMENTS

| 4,757,018 | 7/1988 | Brown. |
| 5,110,737 | 5/1992 | Myoken et al. |
| 5,491,088 | 2/1996 | Hellstrom et al. ............... 435/240.24 |

FOREIGN PATENT DOCUMENTS 2-57184  2/1990  Japan.

PCT/JP93/01723  11/1993  Japan.

OTHER PUBLICATIONS

Kovar, J and Franek, F. Immunology Letters. 7(6): 339–345, 1984.

Iwamoto, K et al. Cytotechnology, 6: 93–103, 1991.

Laskov, R et al. International Journal of Cancer. 48: 574–582. 1991.

Li, Jiliang et al, "Cholesterol requirement for growth of rodent parental myeloma cells in serum free medium", *Journal of Medical Colleges of PLA*, 6(2), 135–40, 1991.

Sawada S et al, "Immunoprotective human monoclonal antibodies against five major serotypes of pseudomonas aeruginosa", *The Journal of General Microbiology*, 133 (12), 3581–3590, 1987.

Jahn S et al, "Cell biology of human igm-producing hybridomas derived from a fusion of human spleen lymphocytes with mouse myeloma cells", *Hybridoma*, 6(6), 679–688, 1987.

Database WPI, Section Ch, Week 9138, Derwent Publications Ltd, London, GB; Class B04, AN 91-277581 XP002007427 & Abstract of JP-A-03 183 477 (Morinaga & Co Ltd), 9 Aug. 1991.

*Primary Examiner*—Christina Y. Chan
*Assistant Examiner*—F. Pierre VanderVegt
*Attorney, Agent, or Firm*—Browdy and Neimark

[57] ABSTRACT

A novel method for production of an exogenous protein is provided, the method being suitable for expression of an exogenous protein, especially a recombinant antibody etc., in an eucaryotic cell by utilizing a genetic recombination technique. That is, a novel method for production of an exogenous protein is provided which allows for culture of a cell in which an exogenous gene is introduced in a serum-free medium and an efficient production of an exogenous protein, by using, as a host cell for expression, a fused cell which is prepared by fusing a mouse myeloma and a lymphatic cell and which can be cultured in a serum-free medium.

10 Claims, 3 Drawing Sheets

GROWTH CURVE AND ANTIBODY CONCENTRATION IN CULTURE SUPERNATANT OF 83-2-10

METHOD FOR PRODUCING EXOGENOUS PROTEIN

This application is a 371 of PCT/JP93/01723, filed Nov. 25, 1993.

TECHNICAL FIELD

The present invention relates to a method for producing an exogenous protein which comprises expressing efficiently an exogenous gene prepared by a genetic recombination, etc. and collecting the expressed protein. Specifically, it relates to an excellent method for producing an exogenous protein wherein the desired exogenous protein, especially a recombinant antibody, is produced by serum-free culture utilizing as a host cell for expression, a fused cell obtained by fusing a mouse myeloma with a lymphatic cell.

BACKGROUND ART

It has been expected to utilize monoclonal antibodies in industry with progress of cell fusion technique in recent years. However, in case of heterogenous antibodies other than a mouse-type antibody, when a heterogenous cell is fused with a myeloma cell line of rodents such as mouse, rat, etc., a phenomenon that a chromosome of said heterogenous antibody disappeared rapidly in a hybrid cell (hybridoma) is observed, and hence, it has been quite difficult to obtain a stable antibody-producing cell. Although cell fusion has also been attempted by using a homogenous myeloma cell line or B cell line other than those derived from rodents, no satisfactory results have been obtained.

On the other hand, with the progress of a genetic recombination technique, cloning of a gene has become easier. As for an antibody, analytical research has been developed at a genetic level, and as a result, it has become possible to isolate and express an antibody gene in a suitable host cell without deletion at a chromosomal level. However, an antibody production level by expression after introduction of an antibody gene was generally smaller than that of a hybrid cell prepared by a cell fusion technique, and hence, this expression method has not been practical. In order to solve this problem, a gene amplification system etc. with a DHFR gene etc. has been used, but in case of a mouse-derived cell system, it is generally said that an exogenous gene is not incorporated into a host chromosome as DM (Double Minutes) and thus instable. There are several reports on a DHFR gene amplification system using a mouse cell but they do not refer to a stability thereof.

A technique for antibody production by the genetic recombination has not been satisfactory in view of an expression system practically usable at an industrial level. Thus, it is desired to develop an excellent method for producing a recombinant antibody both in view of the expression and purification of a recombinant antibody gene.

SUMMARY

Under the circumstances, from the point of a method for producing a recombinant antibody using a serum-free culture, the present inventors have earnestly studied, and as a result, have found that the desired recombinant antibody is quite efficiently prepared by using, as a host cell, a fused cell which is prepared from a mouse myeloma and a lymphatic cell and which can be cultured in a serum-free medium (although such a cell may also be called as a hybrid cell, in the present invention, the characteristic hybrid cell used as a host cell for expression of an exogenous protein is referred to as a fused cell) and expressing an antibody gene in said fused cell, and in this way the present invention has been completed.

There have been reported several methods for producing an antibody by a genetic recombination using a mouse myeloma cell. In the hitherto known methods, however, a parent cell line (myeloma) itself is used as a host cell instead of being used for preparing a hybridoma, an exogenous gene is incorporated into said host cell and the antibody is expressed. However, when a mouse myeloma itself is used as a host cell for expression of an exogenous gene, it is difficult to prepare a cell suitable for culture in a serum-free medium and it deemed to be quite difficult to prepare a host cell which is both capable of growing in a serum-free medium like in a medium supplemented with serum and shows a stable gene expression efficiency.

A representative mouse myeloma cell includes P3X63Ag8.653 cell line. This cell line is an excellent host cell since an exogenous gene can easily be incorporated and it shows a high expression efficiency. However, as mentioned above, the P3X63Ag8.653 cell line is not easily adopted to a serum-free medium, its growth is variable depending on transformants, and hence it can not grow in a serum-free medium but can only grow in a culture medium supplemented with serum. According to the present inventors' studies, this cell line itself shows a cholesterol-dependent autotrophy and a culture medium needs to be supplemented with LDL, YLP (yoke lipoprotein), liposome, etc. for a long subculture. However, even in these culture media containing a high amount of cholesterol, growth is not completely equivalent to that in a medium supplemented with serum and other unknown factors derived from serum are still required. Hitherto, growth factors in serum required by said cell are still unknown.

Thus, the present inventors have fused such mouse myeloma cell with a lymphatic cell to prepare a fused cell which is domesticated so as to be able to be cultured in a serum-free medium, and used the thus prepared fused cell as a host cell for expression of an exogenous gene, and as a result, have found that a transducing cell which expresses a desired exogenous gene efficiently and stably and which is capable of being cultured even in a serum-free medium can be prepared. The lymphatic cell used in the present invention for preparing such fused cell needs to be a cell having a property of adaptability to serum-free culture after fusion. For example, among hybrid cells (hybridomas) generally prepared for production of a monoclonal antibody from a myeloma cell and a lymphatic cell, those cells that were adapted or adaptable to serum-free culture can effectively be used. Among such hybrid cells, a suitable cell for fusion with a mouse myeloma in the present invention includes a hybrid cell Sp2/0 (ATCC No. CRL1581).

The most preferable mouse myeloma to be used for preparation of a fused cell in the present invention includes a mouse myeloma P3X63Ag8.653 cell line (ATCC No. CRL1580). The present inventors have studied in various ways a cell line for use in a preparation of a fused cell being capable of efficiently expressing a recombinant antibody gene, and as a result, confirmed that the above mouse myeloma P3X63Ag8.653 cell line is the most excellent among various mouse myelomas in view of introduction of an exogenous gene.

In order to attain a production of a large amount of an exogenous protein, e.g. a recombinant antibody, on an industrial level, the following conditions should be met:

(1) It can grow in a serum-free medium of low cost in which a desired product can easily be purifired;

(2) It can produce a large amount of a desired product; and (3) It can easily be scaled up in a suspension culture system.

The method for producing an exogenous gene of the present invention using, as a host cell for expression of an exogenous gene, a fused cell capable of being cultured in a serum-free medium prepared by fusing a mouse myeloma with a lymphatic cell is characterized by that fused cells, which are obtained by mixing a mouse myeloma (e.g. P3X63Ag8.653 cell line) with a lymphatic cell and conducting a cell fusion by adding a fusing agent such as polyethylene glycol, are subjected to selection in a serum-free medium and a series of cloning to prepare a fused cell which can grow in a serum-free medium and which can stably express an exogenous antibody gene and said fused cell is used as a host cell, and is an excellent method for production of an exogenous protein in which the desired exogenous gene can be expressed with said fused cell and thereby the desired exogenous protein can be collected from a serum-free medium. The method for production of the present invention satisfies all the above-mentioned conditions.

An exogenous protein to be prepared by the method of the present invention is not specifically limited and includes various useful proteins, for example, an antigenic protein, a physiologically active protein and an enzyme, but in particular, is extremely useful for production of an antibody by a genetic recombination. These antibodies are extremely suitable for expression of various genetically recombined antibodies such as a chimeric antibody, a V region-reshaped antibody [CDR reshaping antibody] etc., and can efficiently produce a desired recombinant antibody.

DETAILED DESCRIPTION

The present invention is explained in more detail hereinbelow by way of example of a production of a recombinant antibody.

Generally, as a basic composition of a culture medium used for a suspension culture of a mammalian cell, RPMI-1640 medium supplemented with 10% fetal calf serum, etc. is usually used. In a serum-free medium having a decreased amount of total protein as shown hereinbelow, the fused cell prepared in accordance with the present invention has a cell growth and a capacity to produce a recombinant antibody equivalent to those in a medium supplemented with serum.

Composition of a serum-free medium

A mixture of Ham F12 medium: Dulbecco modified MEM medium: RPMI1640 medium in a ratio of 1:1:2 or 2:1:1 is used as basic medium and additives as shown in the following Table 1 are added thereto.

TABLE 1

| Additive | Final Concentration |
| --- | --- |
| Transferrin | 1.0 mg/ml |
| Ethanolamine | 0.020 mM |
| Mercaptoethanol | 0.025 mM |
| Selenious acid | 0.013 mg/l |
| Antibiotics | q.s. |
| Mixture of vitamins | |
| Biotin | 2.0 mg/l |
| Calcium D-pantothenate | 2.0 |
| Choline chloride | 2.0 |
| Folic acid | 2.0 |
| Inositol | 4.0 |
| Nicotinamide | 2.0 |
| Pyridoxine hydrochloride | 2.0 |
| Riboflavin | 0.2 |
| Thiamin hydrochloride | 2.0 |

When a DHFR gene amplification system is used, around $10^{-7}$ M methotrexate (MTX) may be added to the medium, and when a G418 resistant gene is incorporated, around 0.5 mg/ml G418 may be added to the medium.

For a lymphatic cell used in the present invention, a normal lymphatic cell obtained from a peripheral lymphocyte, a lymph node or a spleen may be used, but a lymphatic hybrid cell, typically Sp2/0, is suitably used. A cell fusion is conducted by mixing such lymphatic cell with a mouse myeloma cell (preferably P3X63Ag8.653) in the presence of an agent for cell fusion (e.g. polyethylene glycol, etc.) at room temperature. The cell fusion is conducted in a usual manner. For example, 1 to $10 \times 10^7$ cells of P3X63Ag8.653 are mixed with 1 to $5 \times 10^8$ cells of a normal lymphatic cell or with 1 to $10 \times 10^7$ cells of Sp2/0 and the mixture is centrifuged at 1500 rpm for 5 minutes to precipitate cells. After adding serum-free RPMI1640 medium (40 ml), centrifugation is conducted at 1500 rpm for 10 minutes to wash cells. After well dissolving the cell pellet, 45% polyethylene glycol (a degree of polymerization of 1500 to 4000) is added dropwise at a rate of 1 ml per 1 minute and the mixture is stirred gradually for 1 minute. After further adding dropwise 1 ml of RPMI1640 medium over 1 minute and again adding dropwise additional 1 ml of the medium over 1 minute, PEG (polyethylene glycol) is diluted with 8 ml of RPMI1640 medium and a centrifugation is conducted at 1200 rpm for 10 minutes to collect cells. After cell fusion, culture is carried out in a serum-free medium containing 1% fetal calf serum for about 1 week and then in the above-mentioned completely serum-free medium so that P3.653 cell line which did not fuse dies out gradually whereas fused cells keep to grow without destruction. In this way, a fused cell capable of growing in a serum-free medium can easily be obtained and an antibody in a culture supernatant can be screened by a suitable assay such as an antibody labelled with a radioisotope or EIA using an enzyme-labelled antibody etc.

The present invention aims at expressing an exogenous gene, especially a recombinant antibody gene, and hence, a fused cell which does not secrete an antibody derived from the host can be sorted out among said fused cells capable of growing in a serum-free medium by the above-mentioned screening method. Whether the fused cells are suited as a host for a recombinant, however, can be confirmed by conducting the following gene transfection test.

Gene transfection test

Figure 1:
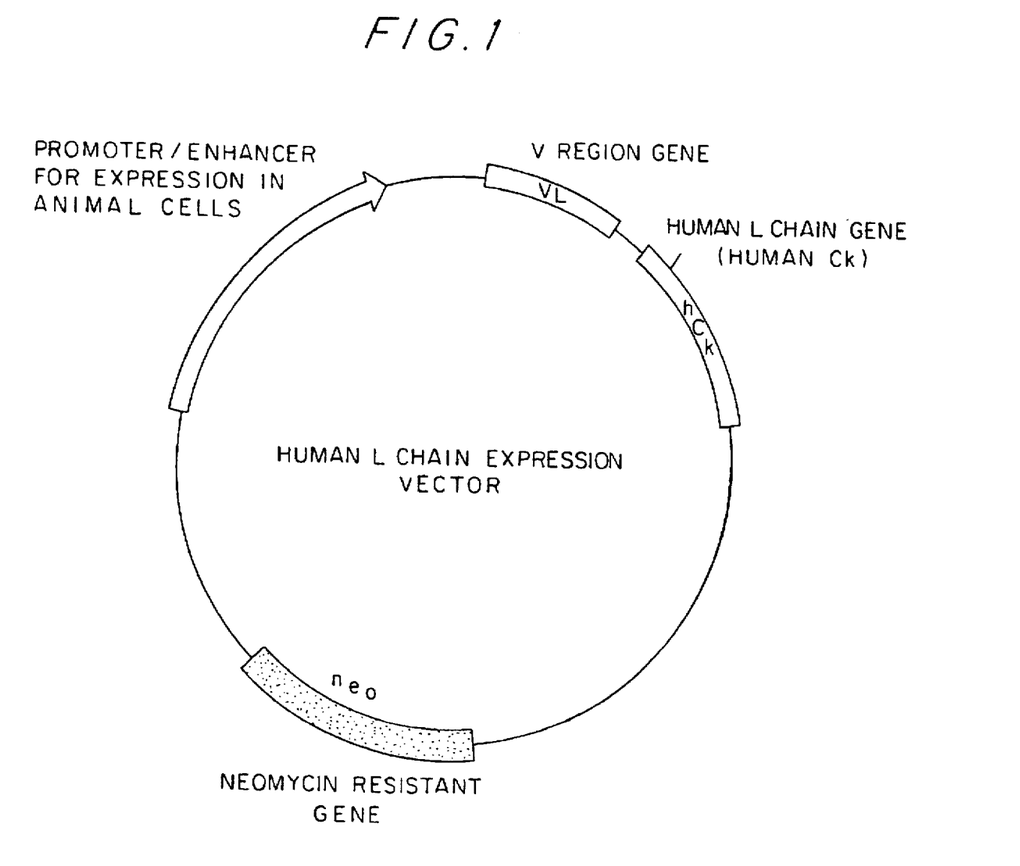
FIG. 1 shows a structure of a vector expressing IgG-L chain by way of example of an exogenous gene used for a gene transfection test.

After conducting a cell fusion in a usual manner and inoculating a suspension of the fused cells in a serum-free medium on a 24-well culture plate, culture is continued for about 2 months while exchanging a culture medium with a fresh serum-free medium for every 3 days. During this culture period, a portion of culture supernatant is taken out and a production of antibody is examined by EIA etc. at 3rd, 14th and 21st day after cell fusion. After about 10 days, pools of fused cells capable of growing in a serum-free medium are obtained and wells showing a good growth are selected and subjected to cloning by a limiting dilution method in RPMI1640 medium containing 10% fetal calf serum. Wells of a single clone are selected and expanded from a 96-well plate to a 24-well plate. When the clones show growth, first a culture medium is exchanged with a serum-free medium containing 5% fetal calf serum and thereafter a concentration of fetal calf serum is gradually decreased and finally switched to a serum-free medium. A cell density of survived wells is counted and the cells are inoculated on another 24-well plate at a density of $2 \times 10^5$ cells/ml and subjected to a gene transfection test. As to the remaining cells, culture is continued in a serum-free medium until test results are obtained. The gene transfection test is conducted wherein the 24-well plate is left to stand until the inoculated cells on the plate precipitate to the bottom of the well, and 0.3 ml of supernatant is removed quietly to set the volume of 0.3 ml/well. A suitable expression plasmid (e.g. a plasmid vector for expression of an antibody L chain, etc. FIG. 1) dissolved in a sterile distilled water and a suitable agent for gene transfection (DEAE dextran, calcium phosphate, lipofectin, etc.) are mixed together to make a total volume of 0.3 ml. After being left to stand at room temperature for 15 minutes, each 0.01 ml of the mixture is added dropwise to the cells on the 24-well plate and the cells are cultured at 37° C. for 5 to 24 hours. After completion of culture, 0.3 ml of a serum-free medium supplemented with 20% fetal calf serum is added and culture is further continued for 2 to 3 days and then the culture supernatant is studied for expression of the gene by using a suitable assay method.

A pool of fused cells showing a high expression efficiency of a desired product is selected and subjected to further cloning by a limiting dilution method using a 96-well microplate and the same gene transfection test is repeated to obtain a fused cell clone suitable for a host of a genetic recombinant.

In addition to the method by introducing an exogenous gene into the obtained fused cell line as mentioned above, it is also possible to first introduce an exogenous gene into a mouse myeloma and the obtained recombinant is then fused with a normal lymphatic cell or another hybrid cell to prepare a genetic recombinant cell aimed by the present invention which is capable of growing in a serum-free medium. That is, introduction of an exogenous gene can be conducted either prior to or after the step of obtaining a fused cell. In case that introduction of an exogenous gene is carried out prior to cell fusion, selection in a serum-free medium is firstly conducted to destroy cells derived from a mouse myeloma (e.g. P3X63Ag8.653) and then culture in a selection medium (containing MTX, G418) supplemented with 1% fetal calf serum is conducted to give antibody-producing cells. The thus obtained cells can gradually be adapted to a serum-free medium. If a large amount of transformant is desired, the method by introducing an exogenous gene after cell fusion is more convenient in order to save labor for cell fusion.

When Sp2/0 cell line etc. is employed as a partner for cell fusion, G418 resistant gene expression unit etc. may previously be introduced into the mouse myeloma P3X63Ag8.653 as a selection marker for fusion and thereby fused cells can easily be selected by culture in a suitable selection medium after fusion. With the use of these agents for gene introduction, it was confirmed that the mouse myeloma P3X63Ag8.653 effectively incorporates an exogenous gene whereas Sp2/0 cells themselves hardly incorporate an exogenous gene.

Figure 2:
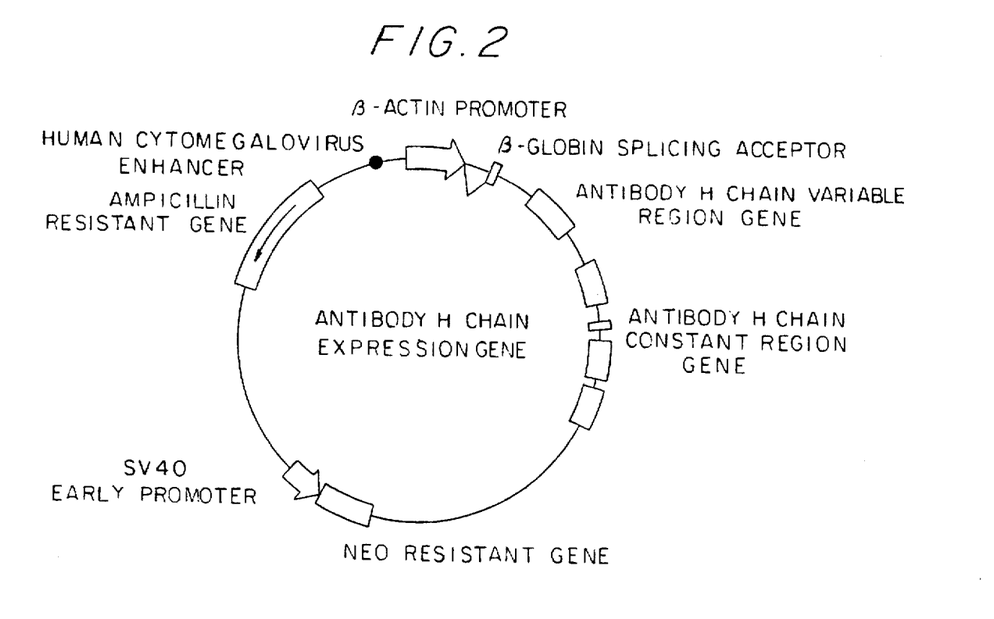
FIG. 2 shows a structure of a vector expressing IgG-H chain used for transformation in Example 4.
Figure 3:
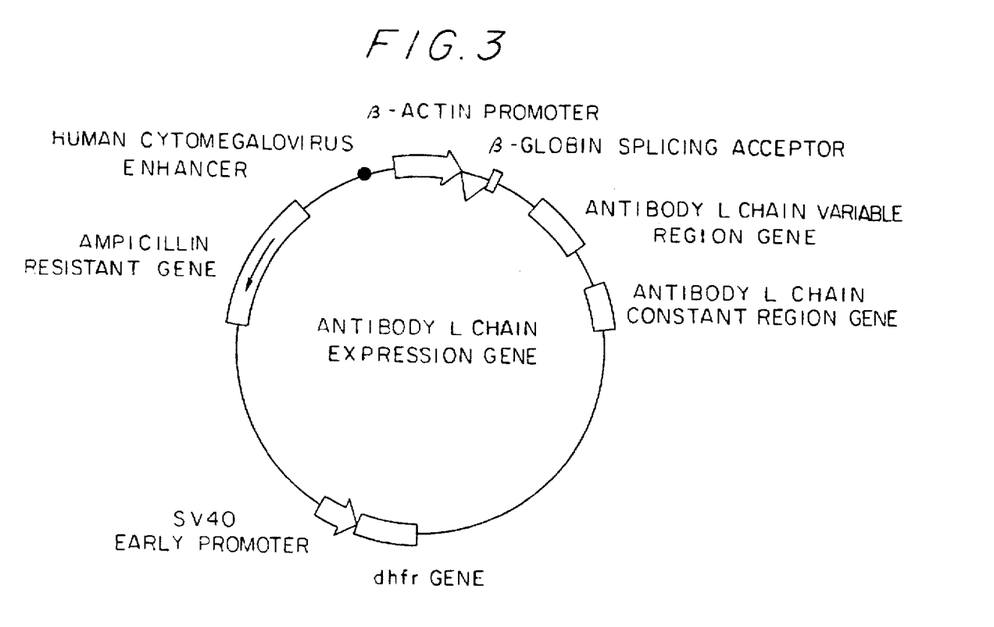
FIG. 3 shows a structure of a vector expressing IgG-L chain used for transformation in Example 4.
Figure 4:
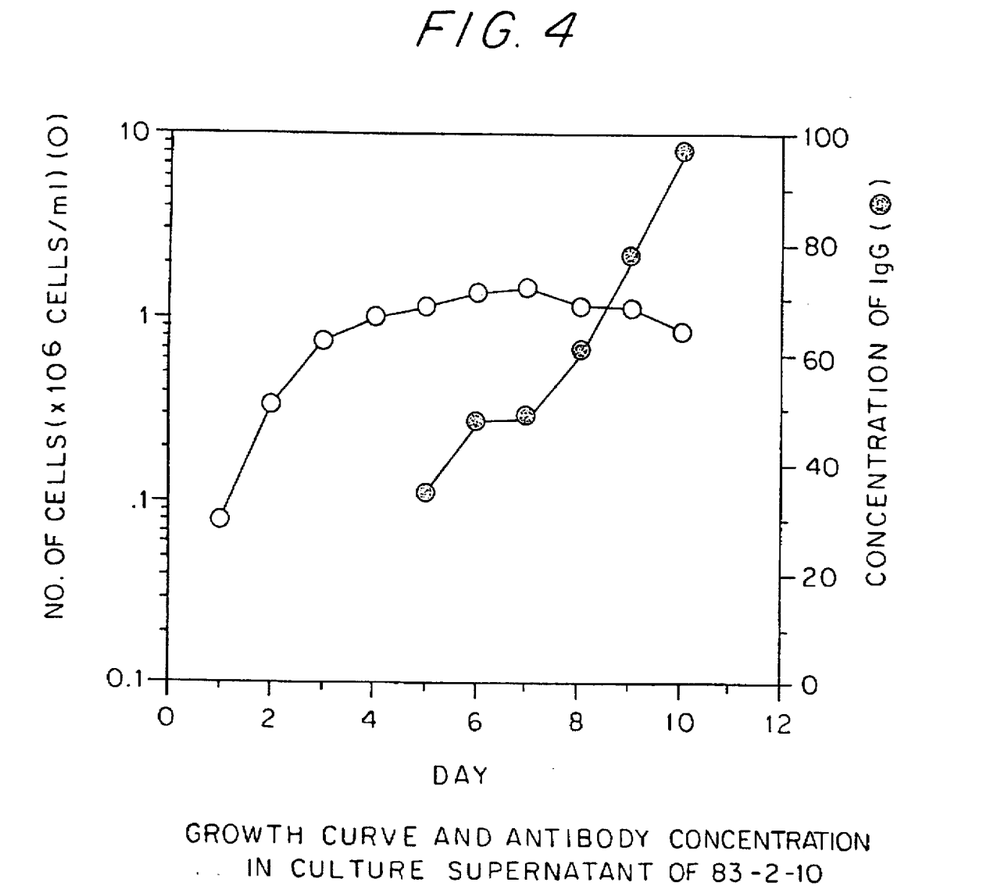
FIG. 4 shows a growth in a serum-free medium of a transformant established by using a fused cell and an expression level.

For use as a host cell for gene transfection, an ability to produce a large amount of a desired gene product is another important factor to be considered in addition to a good transformation efficiency and capability of being cultured in a serum-free medium. Accordingly, it is important to previously assay an expression capacity of a host cell and those host cells having the highest expression capacity should be selected as a host cell. The expression capacity of a cell can be assayed by introducing a suitable gene into the cell to prepare a transformant and then measuring an amount of an expressed product of said gene in a culture supernatant, on a cell surface or within the cell of the transformant. For example, Table 2 shows results obtained by enzyme immunoassay for measuring an amount of a recombinant protein expressed in a culture supernatant of transformants which are prepared by transforming 26 kinds of fused cells and their parent cells (P3X63Ag8.653 and Sp2/0) with plasmids as shown in FIG. 2 and FIG. 3 followed by selection with G418. Most of 26 kinds of fused cells showed higher expression capacity than that of their parent cells and especially the clone No. 34 cell showed the highest production amount. Thus, such clone No. 34 cell was considered to be most suitable for a host cell for expression of an exogenous gene. Using this cell as a host cell, the expression gene as shown in FIG. 4 was expressed to produce as much as 20 pg/cells day of the antibody.

Hitherto, for expression of a large amount of an antibody molecule in a mouse myeloma cell system, another cell culture technique such as by a gene amplification etc. has been required. For example, Gillies et al. (BioTechnology, 7, p799 (1989)) introduced a gene of anti-tetanus toxin antibody into SP2/0 cell to give a transformant and conducted a gene amplification with MTX to increase a production amount by several times. The expression amount by this cell was about 20 pg/cells day/ml. Bebbington et al. (BioTechnology, 10, p169 (1992)) also carried out expression of an antibody gene in a myeloma cell and obtained a transformant having 9.5 to 15 pg/cells day of production capacity, which was also attained by utilizing a glutamine synthetase gene amplification.

A gene amplification is disadvantageous in that firstly it takes time for amplification, usually several months for obtaining a cell line with high expression. A second disadvantage is concerned with a stability of a gene expressed, i.e. deletion of a gene occurred when cultured without a selection reagent such as MTX or MSX, resulting in a decrease of a production amount to that prior to the amplification. Thus, it has been necessary either to add these selection reagents during the culture period or to clone a stable cell line.

On the contrary, the transformed cell derived from the fused cell established in accordance with the present invention had an expression capacity equivalent to that of the above-mentioned established cell lines without need of gene amplification. Hitherto, the present inventors have carried out expression of an antibody gene in P3-X63Ag8.653 or Sp2/0 cell and have found that even those cells having the highest expression capacity could express an antibody at several pg/cells day or less. The present inventors have no precedents of the fused cell prepared in accordance with the present invention having a high production capacity without gene amplification, and this fused cell could firstly allow for such high production capacity. Accordingly, by using this fused cell for transformation, an expression cell having a high production capacity can easily be obtained without need of gene amplification.

It is also possible to further increase an expression level of product of this cell by gene amplification using a reagent such as MTX or MSX. For example, as shown in Example 6, a gene amplification was conducted by increasing MTX concentration during culture of the transformant, and as a result, there was observed an increase in expression of a recombinant protein by at most 10 times.

The present invention is explained in more detail hereinbelow by means of Examples but it should not be construed to be limited thereto.

EXAMPLES

Example 1

A spleen was taken out of a mouse without immunization and spleen cells were sterile suspended in 10 mL of a serum-free RPMI1640 medium. This was transferred to a centrifuge tube to precipitate the connective tissue etc. and a cell suspension of supernatant was collected. To the spleen cell precipitate was added 0.5 mL of a growth medium containing a fetal calf serum and further 10 mL of 10-dilution medium was pipetted quickly and erythrocytes were removed by hypotension treatment at room temperature for 15 to 20 seconds. After hypotension treatment, 10 mL of a two-fold concentrated medium was quickly added, the cells were well suspended with a pipet, additional 10 or 20 mL of a growth medium was added and the mixture was centrifuged (1500 rpm, 5 minutes) to give a precipitate of a spleen cell. Thereto was added 20 to 30 mL of a growth medium and the mixture was well mixed with a pipet and then centrifuged (1500 rpm, 5 minutes, at room temperature) to give normal lymphatic cells. The mouse-derived spleen cells (1 to $5\times10^8$ cells) and P3X63Ag8.653 cell line (1 to $10\times10^7$ cells) were mixed together at a ratio of 5 to 10:1. Thereto was added 40 mL of a serum-free RPMI1640 medium and the mixture was centrifuged at 1500 rpm for 10 minutes to wash the cells. The cell precipitate was well suspended with a pipet and then 45% polyethylene glycol (degree of polymerization of from 1500 to 4000) was added dropwise at a rate of 1 ml per minute and the mixture was stirred slowly for 1 minute. Then, 1 ml of RPMI1640 medium was added dropwise over 1 minute and additional 1 ml of the medium was added dropwise over 1 minute, and then PEG (polyethylene glycol) was diluted with 8 ml of RPMI1640 medium and a centrifugation was conducted at 1200 rpm for 10 minutes to collect cells. After cell fusion, culture was carried out in HAT medium (containing hypoxanthine, aminopterin and thymidine) supplemented with 10% fetal calf serum for several weeks and then in the above-mentioned completely serum-free medium. As a result, P3.653 cell line which did not fused died out gradually whereas the fused cells continued to grow without destruction. As a result, the fused cells capable of growing in a serum-free medium could be obtained.

Example 2

A transformant previously prepared by introducing an antibody expression vector containing a DHFR gene expression unit and a G418 resistant gene expression unit into P3X63Ag8.653 cell line was cell-fused with Sp2/0 cell line (ATCC No. 1581) and selection in a serum-free medium was conducted. The selected fused cells were further cultured in the above-mentioned serum-free medium containing MTX (methotrexate), and after 2 weeks, the presence of an antibody in the culture supernatant was determined by EIA using a peroxidase-labelled anti-IgG antibody. As a result, the transformants which did not fused could not grow in the serum-free medium and died out. On the other hand, the Sp2/0 cell line which did not fused could not grow in the serum-free medium containing MTX and G418 and died out. The fused cells could survive in the serum-free medium containing MTX, and as a result, clones expressing a large amount of a desired antibody could be obtained quite efficiently. Moreover, the cloning in Example 1 was time-consuming since the fused cells had to be cultured in a selection medium such as HAT medium etc. whereas in Example 2, desired clones could be obtained in a short period of time.

Example 3

Mouse hybridoma Sp2/0 cell line is easily adapted to a serum-free medium, and hence, allows for serum-free culture on an industrial scale. Furthermore, since Sp2/0 cell line does not secrete an antibody, a fusion of Sp2/0 cell line with P3X63Ag8.653 can provide a host for introduction of an exogenous gene having the characteristics of both cell lines, i.e. the growth capacity of Sp2/0 and the high gene introduction rate and the high expression efficiency of P3X63Ag8.653.

After cell fusion of both cell lines in accordance with the method of the present invention, culture was carried out in a serum-free medium on a 24-well plate for about 2 months while exchanging the culture medium. Pools showing a good growth were selected and cloning was conducted in RPMI1640 medium containing 10% fetal calf serum. Such well of a single clone of fused cells was selected and expanded from a 96-well plate to a 24-well plate. When growth in a serum-free medium containing 5% fetal calf serum was observed, the culture medium was exchanged with the completely serum-free medium. A cell number was counted for the obtained fused cell clone and the gene introduction test was conducted using lipofectin. As a result, those fused cells which could grow in a serum-free medium and showed an expression efficiency equivalent to that of P3X63Ag8.653 cell line were obtained (Table 2). As a control, P3X63Ag8.653 itself could not grow in the serum-free medium and Sp2/0 could grow but showed an extremely low capacity of antibody production.

TABLE 2

| Clone No. | Secondary screening Anti-hCkEIA: Growth | No. of colony in G418-containing medium |
|---|---|---|
| 6 | .796 +++ | 20 |
| 7 | .174 | 3 |
| 8 | .426 | 14 |
| 10 | .271 | 16 |
| 13 | .188 | 3 |
| 14 | .616 | 3 |
| 16 | .143 | 1 |
| 17 | .053 | 0 |
| 18 | .363 | 0 |
| 20 | .379 +++ | 7 |
| 23 | .065 | 0 |
| 25 | .131 | 2 |
| 27 | .690 | 2 |
| 30 | .111 | 0 |
| 31 | .448 | 18 |
| 33 | .894 | 13 |

TABLE 2-continued

| Clone No. | Secondary screening Anti-hCkEIA: Growth | No. of colony in G418-containing medium |
|---|---|---|
| 34 | 1.529 | 19 |
| 37 | .157 | 0 |
| 38 | .128 +++ | 9 |
| 40 | .336 | 5 |
| 41 | .059 | 0 |
| 44 | .413 | 0 |
| 45 | .720 +++ | 6 |
| 47 | .031 | 0 |
| 50 | .835 | 10 |
| 51 | .274 | 9 |
| P3X63Ag8.653 | .069 | 0 |
| Sp2/0 | .085 | 0 |

Using the fused cells obtained hereinabove, a recombinant antibody gene with a DHFR gene incorporated therein was prepared and the stability of antibody production was studied. The stability of antibody production varies with each clone, but comparatively stable clones among the abovementioned clones did not show decrease in capacity of antibody production even after a large scale culture up to 600 L was conducted in the presence of MTX.

Example 4

The fused cells obtained above was tested for an expression capacity of a recombinant protein. FIG. 2 and FIG. 3 show a structure of expression vectors coding for a recombinant antibody H chain and L chain. Among the fused cells obtained in Example 3, the cell of clone No. 34 was introduced with these two kinds of expression genes. That is, each 10 μg of the antibody H and L chains expression plasmids were mixed with 50 μl of LIPOFECTIN (BRL) and $10^6$ cells was transfected with the mixture. On 3rd day, transformants were selected in RPMI1640 medium containing 1 mg/ml G418, $0.25 \times 10^{-7}$M MTX and 5% fetal calf serum. After selection, transformed cells were cloned by a limiting dilution method to give an antibody-producing cell (named as "8-3-2-10").

This cell was cultured in a serum-free medium and was found to grow well without destruction. As a result of culture on a small scale, a maximum cell density attained was $1.5 \times 10^6$/ml (survival rate 92%) and time required for two-fold multiplication was about 16 hours.

Example 5

A large scale culture of 600 liters in a serum-free medium was attempted for 83-2-10 cells obtained in Example 4. FIG. 4 shows a growth curve of cells and a progress of an antibody level expressed in culture supernatant. This cell could grow well even in a serum-free medium and a maximum cell density attained was $1.45 \times 10^6$ cells/ml. An amount of antibody produced by one cell per day was 20 pg/cells day.

Example 6

By employing the fused cell obtained above, a gene amplification capacity of the expression cell was examined. The expression vectors coding for the recombinant antibody H chain and L chain were introduced into the clone No. 34 cell among the fused cells obtained in Example 3. That is, each 10 μg of the expression plasmids, pSV2-neo incorporated with the gene coding for the antibody H chain and pSV2-dhfr incorporated with the antibody L chain, were mixed with 50 μl of LIPOFECTIN (BRL) and $10^6$ cells of the fused cell were transfected with the mixture. On 3rd day, transformants were selected in RPMI1640 medium containing 1 mg/ml G418, $0.25 \times 10^{-7}$M MTX and 5% fetal calf serum. After selection, the transformed cells were cloned by a limiting dilution method to give antibody-producing cells SP119-2, 3, 7, 10, 15 and 16.

Then, these six kinds of cells were cultured in RPMI1640 medium containing 1 mg/ml G418, $1 \times 10^{-7}$M MTX and 5% fetal calf serum. After one month, an antibody concentration expressed in the culture supernatant of the resistant cell was measured by enzyme immunoassay and compared with that obtained prior to gene amplification. The results are shown in the following Table 3.

TABLE 3

| Name of cell | Rate of increase in antibody production[a] |
|---|---|
| SP119-2 | 1.42 |
| 3 | 2.81 |
| 7 | 7.42 |
| 10 | 2.50 |
| 15 | 10.47 |
| 16 | 1.05 |

[a] A ratio of an expression level of $1 \times 10^{-7}$M MTX resistant cell to that of $0.25 \times 10^{-7}$M MTX resistant cell As is clear from the above results, by increasing the MTX level in the medium by 4-folds and conducting gene amplification, there was observed increase of the antibody expression level by 10-folds in the highest case.

These confirmed that the clone No. 34 cell can well be used for gene amplification.

Accordingly, a higher expression level can be expected by gene amplification of 82-3-10 cell shown in Examples 4 and 5.

INDUSTRIAL APPLICABILITY OF THE INVENTION

For expression of an exogenous gene, especially a recombinant antibody gene, the method for production of the present invention, by serum-free culture, allows for a stable production of a large amount of a desired recombinant antibody etc. in a serum-free medium and makes it quite easy to purify a desired exogenous protein, and hence, there is provided an excellent method for production of an exogenous protein which has hitherto never been reported.

We claim:

1. A method of producing an exogenous protein, comprising the steps of:
    obtaining a fused cell as a host cell for producing the exogenous protein, said fused cell prepared by fusing a mouse myeloma cell and a cell selected from the group consisting of a lymphatic cell and a lymphatic hybrid cell and isolating a fused cell which does not secrete an endogenous antibody of said lymphatic cell or of said lymphatic hybrid cell;
    incorporating an exogenous gene encoding for the exogenous protein into said mouse myeloma cell prior to said step of obtaining a fused cell or into said fused cell after said step of obtaining a fused cell;
    culturing said fused cell having said incorporated exogenous gene in a serum-free medium to express the exogenous protein; and
    collecting the exogenous protein from said medium.

2. The method according to claim 1, wherein said exogenous gene encoding for the exogenous protein is incorporated into said mouse myeloma cell prior to said step of obtaining a fused cell.

3. The method according to claim 1, wherein said exogenous gene encoding for the exogenous protein is incorporated into said fused cell after said step of obtaining a fused cell.

4. The method according to claim 1, wherein said mouse myeloma cell is P3X63Ag8.653.

5. The method according to claim 1, wherein said cell, which is fused with a mouse myeloma cell, is a lymphatic hybrid cell prepared from a myeloma and a lymphatic cell, said lymphatic hybrid cell capable of being cultured in a serum-free medium.

6. The method according to claim 5, wherein said lymphatic hybrid cell capable of being cultured in a serum-free medium is Sp2/0.

7. The method according to claim 1, wherein said cell, which is fused with a mouse myeloma, is a lymphatic cell obtained from a peripheral lymphocyte, a lymph node, or a spleen.

8. The method according to claim 1, wherein said incorporated exogenous gene encoding for the exogenous protein is gene amplified.

9. The method according to claim 1, wherein the exogenous protein is a recombinant antibody.

10. The method according to claim 9, wherein said recombinant antibody has an amino acid sequence in which at least a portion thereof is derived from an antibody of an animal other than mouse.

* * * * *

UNITED STATES PATENT AND TRADEMARK OFFICE
CERTIFICATE OF CORRECTION

PATENT NO. : 5,683,891
DATED : Nov. 4, 1997
INVENTOR(S) : Kiyoto Nishiyama et al.

It is certified that error appears in the above-indentified patent and that said Letters Patent is hereby corrected as shown below:

Cover page, line [86], delete "PCT/JP9501723" and insert therefor --PCT/JP93/01723--.

Signed and Sealed this

Tenth Day of February, 1998

Attest:

BRUCE LEHMAN

Attesting Officer       Commissioner of Patents and Trademarks